United States Patent [19]

D'Aoust

[11] Patent Number: 5,121,627
[45] Date of Patent: Jun. 16, 1992

[54] INTEGRATED MINIATURIZED SENSOR FOR MEASURING TOTAL DISSOLVED GAS AND LIQUID VAPOR

[76] Inventor: Brian G. D'Aoust, 7595 Finch Rd., N.E., Bainbridge Isand, Wash. 98110

[21] Appl. No.: 525,648

[22] Filed: May 21, 1990

[51] Int. Cl.⁵ .............................................. G01N 7/10
[52] U.S. Cl. .................................... 73/19.05; 73/31.04
[58] Field of Search .................. 73/19.05, 31.04, 31.07, 73/720

[56] References Cited

U.S. PATENT DOCUMENTS

| | | | |
|---|---|---|---|
| 4,461,165 | 7/1984 | Kesson | 73/19.05 |
| 4,463,593 | 8/1984 | Parker | 73/19.05 |
| 4,656,454 | 4/1987 | Rosenberger | 73/720 X |
| 4,662,210 | 5/1987 | D'Aoust | 73/19.05 |
| 4,702,102 | 10/1987 | Hammerton | 73/19.05 X |

FOREIGN PATENT DOCUMENTS 1315837  6/1987  U.S.S.R. ............................. 73/31.04

*Primary Examiner*—Tom Noland
*Assistant Examiner*—Joseph W. Roskos

[57] ABSTRACT

Pressure sensing device having a housing (12) with a bottom wall (14) and interior surface (16) and having upstanding edge wall (18) around the periphery of said housing (12). A layer (22) supports a pressure sensing element (30) and its circuitry. A porous gas permeable support layer (40) overlies said pressure sensing element (30) and includes a gas chamber (42) adjacent to the pressure sensing element (30). A gas permeable membrane (50) is supported on said support layer (40). The elements are sealed with respect to the housing as is wire or cable (32) leading from the pressure sensing element (30) to instrumentation remote from the sensing device for readout of measurements by the sensor device (10).

27 Claims, 2 Drawing Sheets

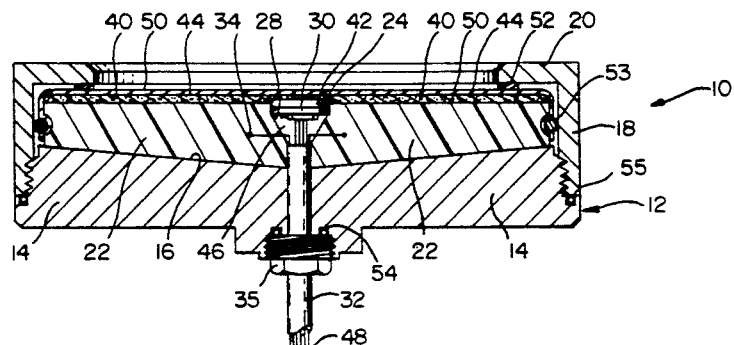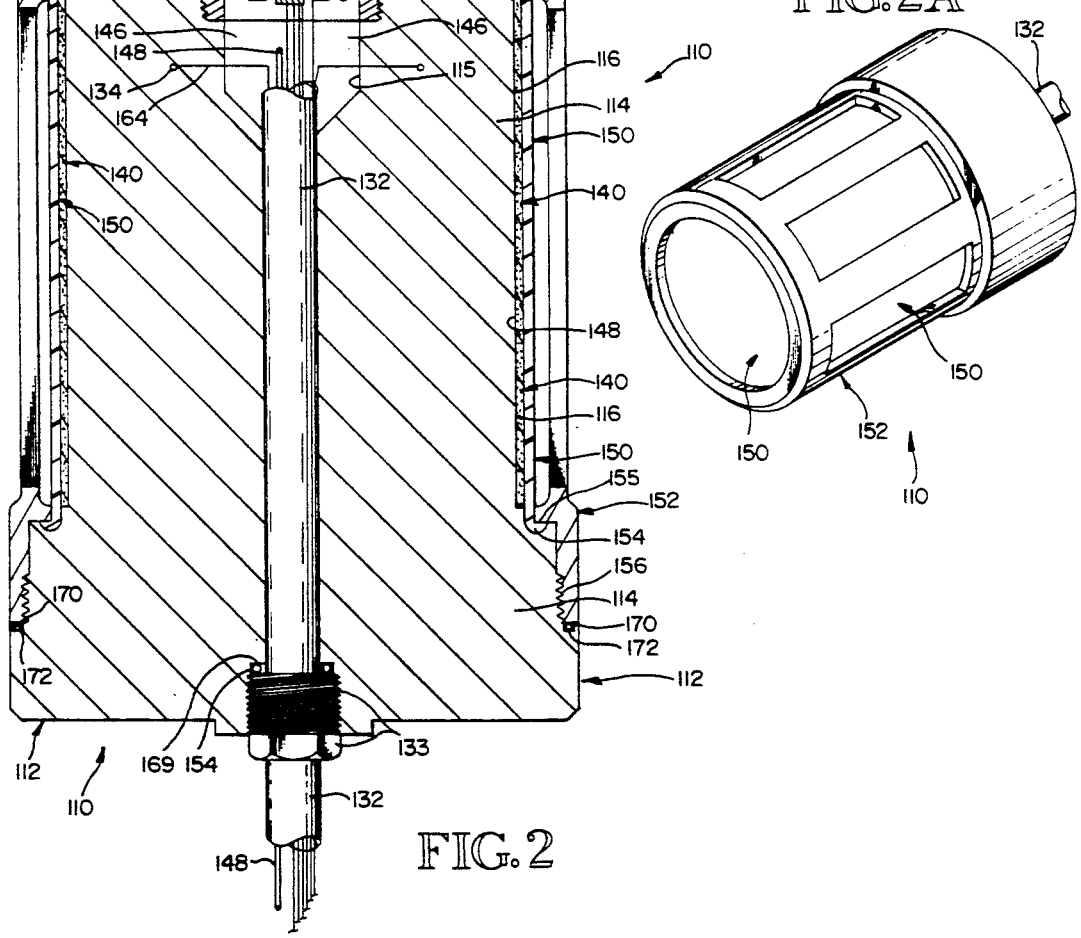

INTEGRATED MINIATURIZED SENSOR FOR MEASURING TOTAL DISSOLVED GAS AND LIQUID VAPOR

TECHNICAL FIELD

The invention relates to the field of instruments, methods and techniques for measuring the total pressure of gases dissolved in a liquid, solvent solution or slurry and more particularly to a new device for measuring total dissolved gas and liquid vapor pressure in which the sensing means and support structure are an integrated component.

BACKGROUND ART

The determination of total and partial gas pressures in water and other liquids provides valuable information as to the degree to which equilibrium with the gaseous environment or the atmosphere has been established, and the differential gas pressure between the solution and its environment. For the purposes of this discussion and description, total dissolved gas pressure in a liquid means the sum total of all partial pressures of gases dissolved in the liquid including the vapor pressure of the liquid. In other words it is a direct evaluation of Dalton's Law for a mixture of gases but performed in a liquid. This parameter is of importance in many areas. Studies to determine relationships between excess pressures and environmental conditions which have created supersaturation problems require the measurement of total dissolved gas pressure. It is an indication of saturation state which has importance in hydrology, fisheries, aquaculture and industry.

Fish and aquatic life in rivers, lakes, hatcheries, aquaria and other aquaculture projects have often died either for lack of oxygen from deficient saturation or from gas embolism because of the excess total pressure of dissolved gases in these various bodies of water. Such conditions facilitate bubble formation in the organisms, similar to air embolism in divers, and often with fatal results. As a consequence, instruments capable of quickly and easily providing and automatically monitoring the dissolved gas pressure information are currently used and increasingly needed to monitor waters where there is any likelihood of danger or risk to fish and aquatic life.

As those skilled in the art are aware, water in which there is as little as 10 percent excess of dissolved gas can be stressful or lethal to fish. Any pumped or otherwise pressurized water supply can present a risk and hence it is necessary to know the levels of air dissolved gases in a particular system. In addition, many industries aerate or sparge water or other fluids with air or other gases to saturate with or remove other gases. Measuring techniques and new sensors such as that herein described will facilitate economical quality control where used.

At the present time no industrial grade sensors exist suitable for this purpose with the exception of those mentioned above which were primarily designed for fisheries and aquaculture and which have several accompanying deficiencies.

Individual instruments and techniques for measuring dissolved gas and fluid vapor pressures in solutions have for the most part been concerned with particular gaseous components. Some of the more obvious applications of a device for measuring total dissolved gas pressure are in the area of water pollution, industrial and other waste water analysis, fish hatchery water quality, aquarium water quality, and wine, beer and beverage production. There are other applications where it is desired to assess the state of gas pressure equilibrium or disequilibrium between the water or fluid and a gas phase. Accordingly, the invention's application to water quality is an obvious example of general applications requiring knowledge of the saturation state of any liquid with respect to ambient hydrostatic pressure and with respect to atmospheric pressure. Clearly, these more general uses include numerous industrial, research and even space applications and provide a new analytical method of greater simplicity and convenience.

Current state of the art instrumentation is unnecessarily cumbersome and expensive. Some of the prior non-electronic instruments, sometimes referred to as "saturometers" or "gasometers" require time consuming and tedious procedures, sometime require water pumps, and as a result present prohibitive disadvantages if a large number of measurements must be taken to monitor a relatively large body of water, or if remote measurements or measurements at depth must be made. Additionally, known instruments and their use in the field require skill in and training for the operators, are susceptible to membrane damage and are time consuming to repair.

Also such instruments do not provide an absolute pressure reading but only a gauge or differential pressure which due to barometric pressure fluctuations prevents calibration of percent saturation and is subject to physical constraints. Furthermore, the use of dial gauges employing a Bourdon tube with a considerable internal volume imposes further equilibration time requirements and gradual gauge errors due to corrosion. Further, the alternative of using mercury in an open-ended manometer while having the advantage of providing a true differential reading increases the size of the devices using it, involves positional constraints and always involves environmental and health hazards if spilled. Such instruments also will require an operator or observer at the measuring site which increases the cost of measurements and eliminates the utility of the devices in automatic process control.

The existing instrumentation for performing the measurement of total dissolved gas pressure, including the devices described in the patents infra, have the disadvantage of requiring knowledge and experience of a specialist in making the required measurements. All the previous devices require tedious disassembly for replacement of the sensing membrane if it is punctured or otherwise damaged or blocked. Such prior art devices are limited in this respect by the large amount of silicon rubber tubing needed to overcome their internal volume and the slow response time. Commercially available models are also limited by the amount of silicon rubber tubing which can be interfaced with the pressure transducer and still allow both ease of changing the membrane, and a reasonable equilibration time. The instant invention overcomes these disadvantages by being more amenable to rapid total replacement or rapid membrane repair.

Current state of the art instrumentation is shown in U.S. Pat. No. 3,871,228; U.S. Pat. No. 4,366,700; U.S. Pat. No. 4,563,892; and U.S. Pat. No. 4,662,210. The last patent listed measures multiple parameters but its utility is limited because of the size of the sensor probe, relatively slow speed of response, replacement expense, eventual condensate formation inside the tubing and manufacturing and maintenance costs. Additionally in U.S. Pat. No. 4,662,210 the apparatus requires separate configuration of the membrane tubing separating the water from the gas phase and connection of this by means of a type of narrow tubing placed through a waterproof housing to the pressure sensing device. The waterproof housing equipped with a feed through to connect to the housing contains the pressure sensor which must be chosen for minimal internal volume. Choices of pressure sensors with low internal volume are necessarily limited and those that are available are often of a shape or configuration which does not facilitate compact or convenient design of the resulting probe. Also many of the most sensitive pressure sensors involve a large surface area which increases internal volume when interfaced with such tubing. In particular, the size of the probe limits its application where small size is necessary. Also, replacement costs are high and some labor of specialized personnel is required. A further shortcoming of existing methods including the listed patented systems is the potential for formation of liquid condensate inside the lumen of the dimethyl silicon tubing. The condensation can reduce the accuracy of the pressure reading as cross bridging of pure liquid drops inside the capillary causes meniscal forces to affect the total gas reading.

Thus, it becomes apparent that the preferred approach to overcoming the difficulties discussed above is an integrated design as set forth and claimed hereinafter.

DISCLOSURE OF THE INVENTION

The instant device is a single sensor for the direct measurement of total dissolved gas and vapor pressure in a liquid. The device integrates an absolute, gauge or differential pressure sensing strain gauge using either a piezoelectric or piezoresistive bridge or capacitive pressure sensing circuit with a porous support structure and membrane permeable to gases to provide a sensor sensitive only to dissolved gas pressure. In contrast to prior art the porous support structure and pressure sensor are well integrated to reduce internal gas volume in order to provide the most rapid response. The total sensor includes a housing of metal or plastic material in which is located a rigid but porous silicon, ceramic, plastic or sintered metal mounting wafer which supports on its outside the gas permeable membrane and against which on its opposite side is intimately opposed the integrated electronic pressure sensor. Next to the porous membrane support is the highly gas permeable membrane including means to adhere it to the porous support. A small gas chamber of minimal volume is formed on the inside of the porous support immediately adjacent to the pressure sensor's diaphram or pressure sensitive surface. Linearizing circuitry is included with the transducer and a signal line exits the housing through a liquid proof seal to the instrument readout. The gas phase side of the sensor is sealed with respect to the water or fluid in which the device is used, and in the absolute pressure version, the opposite side of the pressure sensor is referenced to a zero pressure or vacuum chamber.

Accordingly it is among the many features and advantages of the invention to provide a new and novel device for integrating and interfacing a gas permeable membrane with a hydrostatically incompressible but gas permeable support and pressure sensor or pressure sensitive wafers to allow the measurement of total dissolved gas and vapor pressure in liquids, and to accomplish this with a small compact device. The device greatly extends the application of the direct methods for sensing total dissolved gas and liquid vapor in liquids. Furthermore, the invention overcomes all of the difficulties of prior devices, virtually all of which use a small gas permeable dimethyl silicon rubber tube as both the liquid phase and liquid pressure isolation means. By intimately configuring this gas permeable membrane of the instant invention with a porous mechanical support of minimum gas volume together with the pressure sensing element, a variety of membrane and housing configurations are available which are suited to various applications of the device. In particular reduction in size is possible.

In mounting the membrane on the porous support or spacer to provide mechanical rigidity against hydrostatic pressure and uniting the pressure sensitive element intimately with the opposite side of the porous spacer material there is achieved an integrated design amenable to modern production techniques. The integrated design accomplishes the same functions of prior art devices without the need for large lengths of tubing, and awkward and cumbersome waterproof housings for the pressure sensors. The device is constructed so that the pressure sensing element is intimately joined and mechanically strain-relieved next to a small gas volume of no more than a few cubic millimeters or less so that only the pressure of the gas is sensed. Additionally, the small gas volume communicates with a large surface area of the highly permeable membrane which is also strain-relieved by the rigid gas permeable and porous membrane support material which also houses the pressure sensing element(s). The problem of condensation inside the tubing used in the prior art is alleviated by including in the device a small heating element requiring only a few microwatts of power to raise the internal temperature, thereby preventing condensation of water or other vapor, since the temperature inside the device is always slightly higher than that outside in the sensed fluid.

The invention eliminates the awkward size and design of prior art devices, greatly increases the speed of response, reduces replacement expense, eliminates condensate formation and greatly reduces manufacturing and maintenance expense. As such it becomes an industrial grade sensor with a large number of new applications.

BRIEF DESCRIPTION OF THE DRAWINGS

FIG. 1 is a cross section view in elevation illustrating the arrangement of elements in a generally flat configuration of the invention;

FIG. 2 is a cross section view of a round or cylindrically shaped embodiment of the invention;

FIG. 2A is a perspective view of the device of FIG. 2; and

BEST MODE FOR CARRYING OUT THE INVENTION

Figure 3:
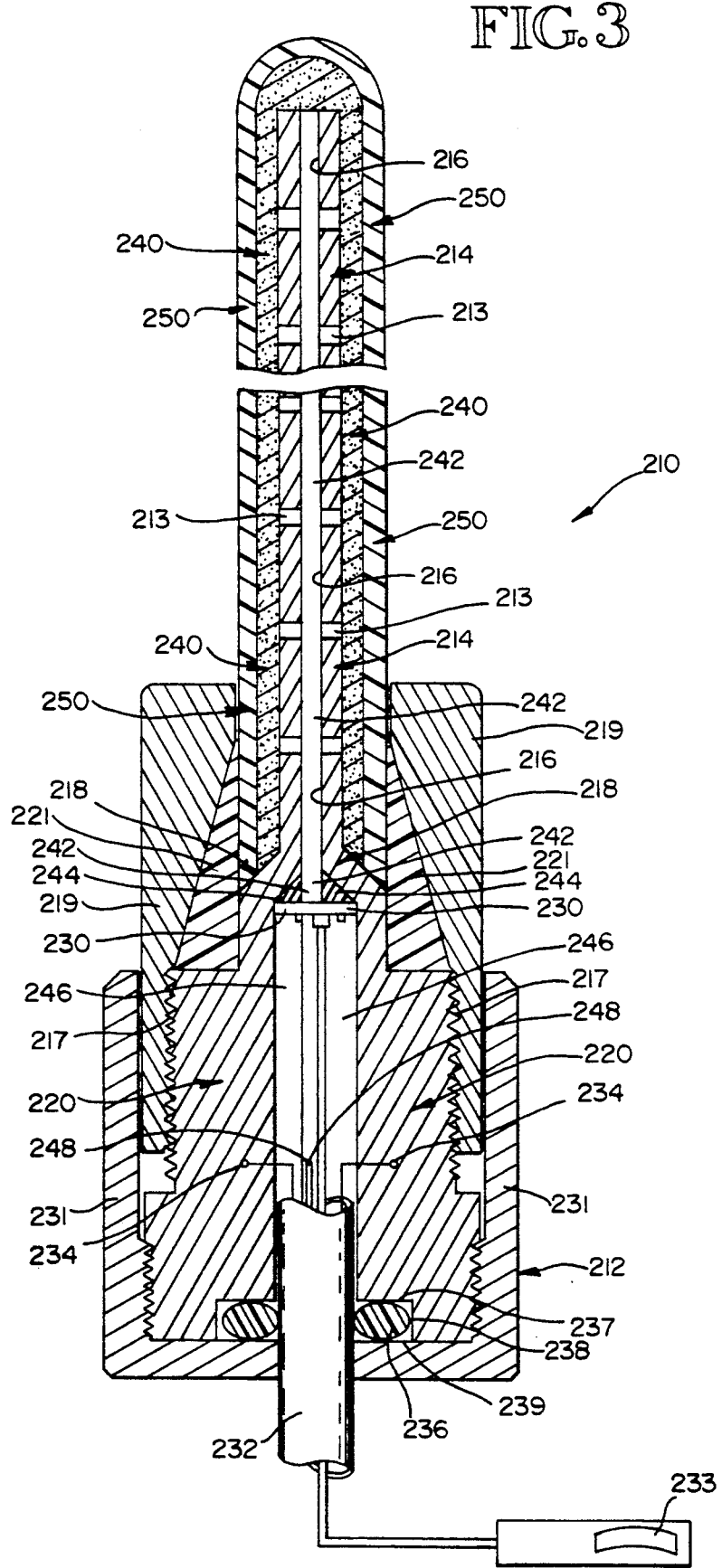
FIG. 3 is a cross section view of an elongated rod or needle embodiment of the invention.

Referring now to the drawing of FIG. 1 it will be seen that the sensor device, generally designated by the number 10, has a circular housing 12 which is shown to have a bottom wall 14 with interior support surface 16, upstanding shallow annular side wall 18 around the entire periphery of bottom wall 14, and, when required for membrane positioning, an inwardly extending annular lip or ledge 20 at the top of side wall and annular retainer nut 18. Housing 12 is preferably made of a stainless steel, anodized aluminum, plastic or ceramic waterproof material.

On the inside surface 16 of bottom wall 14 is installed a support disc 22 for support of the pressure sensing means 30 which is in the form of a piezoresistive or piezocapacitive pressure transducer and/or integrated linearizing circuitry 30 on a single wafer, and for support of porous support 40 and membrane 50. Sensor 30 can be either a monolithic or hybrid pressure sensing device and is designed to function with respect to a minimum volume 42 as an important constraint. Close integration of such pressure sensing means with both porous support 40 and support disc 22 is thus an important constraint to achieve minimum volume 42. The pressure sensitive element is designed so as to be intimately interfaced with the minimal gas volume which is continuous with the porous support and is herein referred to variosuly as "pressure-sensitive means", "pressure transduction system", "integrated electronic pressure sensor", "pressure sensitive wafer" or "pressure sensor" depending on the embodiment being described or discussed. Modern integrated circuit and pressure sensor design allows this intimate interfacing.

It will be noted that an enclosed gas volume 46 is provided centrally and to the rear of the pressure sensitive wafer 30 defined by upwardly and inwardly angling wall surface 28 which terminates near the top of the wafer. It is to be understood that the volume 46 behind the pressure sensitive wafer 30 is separate and distinct from the minimal volume 42 which is sensed by the pressure sensitive wafer 30. The pressure sensitive wafer 30 is joined to and supported by ledge support surface 24 of lower support disc 22 at the top of the conical or angled wall 28 where a gas-tight seal is made. As stated above, the pressure sensor and integrated circuitry 30, which includes the linearizing circuitry and heater element, is connected via line 32 to a suitable instrument readout which accepts either a current proportional or voltage proportional signal. It will be appreciated that line 32 is sealed in a waterproof manner with respect to housing 12 by means of nut 35 and O ring 54 or other means of sealing such as by potting compound.

The porous membrane support member 40 lends rigidity and firm support for a membrane 50 to be discussed in greater detail hereinafter. The porous membrane support member 40 in turn is supported by disc 22 on the surface 16 of bottom wall 14. The porous support member 40 limits any mechanical deformation of the membrane and consequent pressure increase in gas volume 42. The elements 22 and 40 may be one component of two different porosities such that the lower part 22 is not porous and the upper part 40 is porous. This allows further integration and reduction in volume 42. The chamber 42 is small and only of sufficient volume to allow sensing of the total gas pressure by sensor 30 with no possibility of mechanical distortion of the porous support 40 which would be sensed by sensor 30.

Membrane support 40 is made of a non-compressible porous materials: for example glass, plastic, sintered metal, porous aluminum oxide, porous silicon or ceramic material providing enough porosity to allow gas flow. It will be appreciated that the total gas volume of membrane support 40 and chamber 42 must be minimal, that is on the order of a few cubic millimeters or less.

Membrane 50, supported on the generally flat planar top surface 44 of membrane support 40 and sealed at its circumference by compressed seals 52 and 53, is preferably made of dimethyl silicon which is a material highly permeable to the gases and liquid vapor from the liquid environment in which the device is used. For harsh environments or higher temperatures membrane 50 should be of material with appropriately increased physical properties. It will be understood that the top surface of membrane support 40 may be slightly rounded if desired to accomplish a slight tension in membrane 50 to insure its intimate contact with the entire surface of porous support 40. This is to prevent both unwanted extra gas volume 42 and free motion or movement of membrane 50. Another means of accomplishing this constraint is an adhesive bonding of membrane 50 and surface 44 so that no significant barrier to defusion is imposed. The gases diffuse through the membrane into the sensed gas volume area 42 according to their partial pressures in the liquid sensed. The entire device is sealed from penetration by the external liquid environment by the housing 12 which has provision for liquid proof sealing as by seals 52 and 53 around the periphery of membrane 50 and seals 54 and 55 for the lead wire 32 and annular nut or side wall 18. This is accomplished by annular nut 18 being sealed with "O" rings 53 and 55 respectively while at the same time sealing membrane 50 at its circumference with seal 52 in the shape of an annular gasket.

The opening or larger volume area 46 defined by the wall surface 28 behind the pressure sensing element 30 can be evacuated to 0 pressure to provide a true absolute pressure reading or an absolute pressure sensor 30 can be provided which embodies its own zero pressure reference chamber. The small tube 48 exiting with cable or line 32 is optional and is used in an embodiment of the invention in which the pressure sensor 30 acts as a differential or gauge rather than an absolute pressure sensor.

Since dissolved gas in a fluid is being sensed the sensor 10 must be designed and engineered so that hydrostatic pressure cannot transfer mechanical stress to the pressure sensing elements in any way which would result in erroneous pressure readings. Thus it is important that the membrane 50 and its support member 40 are sufficiently rigid to avoid transmitting "noise" to the sensor so that stable readings will result. Similarly all parts fit together with minimal tolerances. The small gas volume of the membrane support 40 and gas chamber 42 combined with the thin membrane 50 which is approximately 0.001 inches thick, enables a rapid response time for obtaining a reading.

The response time of some of the above discussed prior art devices may be in the order of 10 to 20 minutes. This is because of both a relatively high internal volume in relation to the membrane surface area and a relatively thick membrane in the order of 0.006" through which the gases must diffuse. The instant device therefore lowers the equilibration or response time by using a thinner membrane which allows a faster gas flux, and minimizes the internal gas volume by means of porous support 40 and mounting or integrating the pressure sensing wafer onto the rear of the membrane support 40. Response time, as will be appreciated, is inversely proportional to membrane surface area of contact and directly proportional to membrane thickness and internal gas volume, including that of the interstices of porous support 40. Thus, the lower the internal volume and the larger and faster the membrane the shorter the response time. It will be understood that having the exposed gas-diffusing area, when expressed in square centimeters. much larger than that of the gas phase contacting the pressure sensor, when expressed in cubic millimeters, allows maximal surface area to volume ratio. In order both to provide maximum surface area to volume ratios and to a accommodate different applications, alternative membrane configurations are possible and are shown in FIGS. 2 and 3. These are not inclusive of the possible forms but illustrate various alternative embodiments which may be used for different applications of the device. In each embodiment pressure sensor design is optimized for intimate connection to the gas volume 42, 142 and 242.

In FIGS. 2 and 2A a "drum" or cylindrical configuration is shown in which the housing 112 has cylindrical wall 114 enclosing a central cavity 117 defined by interior surface wall 115. Housing wall 114 has exterior support surface 116 and end wall surface 118. In this embodiment the pressure sensitive means 130 is supported on surface 122 of the threaded housing insert 121 which threads into housing 114 by threads 123. Lead wire or cable 132 extends from the pressure sensor circuitry on the underside of the wafer 130 into cavity 146, in which is housed the power supply for heating elements 134, which heat housing 114, and thence exits housing 112 by means of packing gland 133 and "O" ring 135 so that the interior of the sensor remains sealed from the external liquid environment.

As will be seen by reference to FIG. 2 the porous membrane support member 140 is shaped like a cup having a closed end wall 141 abutting support surface 118 and including gas chamber 142 formed next to the pressure sensor 130. The internal surface 148 of the porous membrane support 140 is supported by surface 116 of the main housing 114, thus defining the cup shape as mentioned above for support of the membrane 150 which is also cast in a cup shape. A cap and membrane locking cage 152 is located on the outside of unit 110 and screws onto it by means of threads 156. This insures firm seating of each end of the membrane against porous support 140. This in turn insures that no gas phase is allowed between porous support 140 and membrane 150. The rear end of cast membrane 150 is provided with a bead 154 for sealing purposes between external surfaces of the housing 114 and the flange surface 155 of cage 152. Thus, the end of the cylindrical cage maintains the seal of membrane 150 and porous support 140.

The pressure sensor 130 is mounted on an annular threaded mounting ring 121 by means of a gas tight seal on surface 122 achieved by epoxy cement or other incompressible means. The heater 134 for housing 112 is powered by electrical supply lines in cable 132. As in FIG. 1 a packing gland nut 133 compresses "O" ring 154 against surface 169 and "O" ring 170 against surface 172 to allow leak-proof exit of wire 132. As in FIG. 1 tubing 148 is optional for differential or gauge types of sensors.

A third configuration generally designated by the number 210 is shown in FIG. 3 and is seen to take a rodlike or needle shape which includes housing 212 having elongated needle portion 214 with a very small bore 216 in the order of 0.002 to 0.003 inches in diameter. A number of openings 213 extend from the outer surface of the needle portion 214 to inside surface 216 to permit movement of the gas to the gas volume space 242. Needle portion 214 is part of intermediate housing section 218 which in turn is part of housing base portion 220. As can be seen, a gas porous layer 240 is supported by the stiffener portion 214 and the membrane 250 in turn is supported on the porous layer 240. Threads 217 are located on the base portion 220 to receive tubular retaining nut 219 which exerts pressure on compressible ferrule 221 which in turn exerts sealing pressure on membrane 250 to effect a seal between the liquid phase outside of the device and the gas phase 242 on the inside of the device.

A second nut 231 which is cup shaped threads on to the back of housing base portion 220 and bears on "O" ring 236 to seal on surfaces 237, 238 and 239 the liquid phase from intruding on the gas phase around wire 266. If needed a heating element 234 may be included in the base of the housing particularly if the device 210 is to be immersed for long periods of time.

It will be seen that bore 216 of the needle portion 214 is continuous and extends through epoxy seal 244 to one side of the pressure sensing means 230 supported by epoxy mount 244. An internal volume or chamber 246 is established behind the pressure sensing means 230. Thus, it will be appreciated that the bore 216 comprises the minimum gas volume space 242 which the pressure sensing device will detect and read and signal to the controls via wire leads 232. A vent tube 248 may be included in the cable pack 232 as with the other embodiments to accommodate use of a differential or gauge pressure sensor means.

Again, the configuration of FIG. 3 is designed to minimize the gas volume area 242 like 42 and 142 in the other embodiments, and to provide hyrostatic pressureinsensitive support for membrane 250. Gas volume 242 appears larger in this embodiment than in FIGS. 1 and 3, but this is due to convenience in illustration rather than a requirement of the configuration.

The configuration of FIG. 2 relies on the same structural principles as FIG. 1 yet assumes a shape which could be convenient in liquid flow through applications as for instance conduits or pipes or other duct means.

The possibility of condensation of the sensed liquid vapor such as water vapor inside the sensor device is another consideration in the design of the instant device. Thus a small heating element such as 134 in FIG. 2 which is able to supply a few microwatts of heat to raise the temperature in the gas phase above that of the liquid sensed will render vapor condensation impossible.

As stated above optimization of the performance of the device requires that the pressure sensing component be as intimately integrated with the porous support member as possible. Such intimate integration implies specific manufacturing techniques for sensors 30, 130 and 230 and would even include the further refinement wherein the material which physically houses the pressure sensitive wafer 30, such as silicon substrate, be of variable porosity so that it could also be the material used in the porous support 40 thereby allowing even more integrated configurations of elements 30 and 40 which would achieve even further reductions in internal gas volume.

It will be appreciated that the vent tubes 48, 148 and 248 in the illustrated embodiments will attach directly to the pressure sensor in the event a differential or gauge pressure sensor means is used and will extend to the liquid medium or to the atmosphere.

I claim:

1. An improved sensor device for measuring total dissolved gas and liquid vapor, comprising:
   a) a water proof housing of predetermined shape which supports a pressure sensitive wafer means,
   b) pressure sensitive wafer means including integrated circuitry for required signal supported in said housing and including mounting means for mechanical support and a pressure sensor supported on said mounting means, said pressure sensor being connected by connecting wire means for transmitting signal extending through said housing in sealed relationship thereto to an instrument and instrument readout means for indicating total dissolved gas and liquid vapor pressure,
   c) a gas porous, mechanically rigid membrane support layer, said membrane support layer overlying and being integrated with said pressure sensitive wafer means including a gas chamber of predetermined minimum volume adjacent said pressure sensitive wafer means such that said pressure sensitive wafer means is spaced from direct contact with said membrane support layer to assure that only gas pressure is sensed by said pressure sensor,
   d) gas permeable membrane means supported on and by said gas porous membrane support layer such that dissolved gas and liquid vapor of a liquid diffuse through said gas permeable membrane means into said porous membrane support layer and into said gas chamber so that gas pressure in said porous membrane support layer reflects the total gas and liquid vapor pressure in the liquid and is sensed by said pressure sensor,
   e) said pressure sensitive wafer means, said porous membrane support layer, and said gas permeable membrane means being liquid sealed with respect to said housing to that liquid in which the sensor device is being used is prevented from entering said device, whereby only dissolved gas and liquid vapor diffusing through said gas permeable membrane means are sensed by said pressure sensor and a signal is generated by said integrated circuitry and transmitted to said readout means remote from said pressure sensitive wafer means.

2. The improved sensor device according to claim 1 and wherein said housing includes central opening means therethrough so that a sealed cavity is defined on one side of the pressure sensitive wafer means opposite said gas chamber so that said connecting wire means is able to connect to said integrated circuitry for said pressure sensitive wafer means.

3. The improved sensor device according to claim 2 and wherein said heating element means is provided within said housing and within said sealed cavity to prevent the formation of condensation.

4. The improved sensor device according to claim 2 and wherein said pressure sensor is a piezoresistive pressure transducer.

5. The improved sensor device according to claim 2 and wherein said pressure sensor is a piezocapacitive pressure transducer.

6. The improved sensor device according to claim 1 and wherein said pressure sensor is a piezoresistive pressure transducer.

7. The improved sensor device according to claim 2 and wherein said pressure sensor is a piezocapacitive pressure transducer.

8. An improved sensor device for measuring total dissolved gas and liquid vapor, comprising:
   a) a water proof housing of generally cylindrical shape having an outer cylindrical support surface and an end support surface, said housing further having a cavity therein opening onto said end support surface to define space for receiving a pressure sensitive wafer means, said housing also including a rear portion at the end thereof opposite said end support surface,
   b) pressure sensitive wafer means including integrated circuitry for required signal supported in said cavity in said housing and including mounting means for mechanical support and a pressure sensor supported on said mounting means, said pressure sensor being connected by connecting wire means for transmitting signal extending through said housing and said rear portion in sealed relationship thereto to an instrument and instrument readout means for indicating total dissolved gas and liquid vapor pressure,
   c) a gas porous, mechanically rigid membrane support layer overlying said housing cylindrical support surface and end support surface to define a cup shape, said membrane support layer overlying and being integrated with said pressure sensitive wafer means including a gas chamber of predetermined minimum volume adjacent said pressure sensitive wafer means such that said pressure sensitive wafer means is spaced from direct contact with said membrane support layer to assure that only gas pressure is sensed by said pressure sensor,
   d) gas permeable membrane means supported on and by said porous membrane support layer such that dissolved gas and liquid vapor of a liquid diffuse through said gas permeable membrane means into said porous membrane support layer so that gas pressure in said porous membrane support layer reflects the total gas and liquid vapor pressure in the liquid and is sensed by said pressure sensor,
   e) said pressure sensitive wafer means, said porous membrane support layer, and said gas permeable membrane means being liquid sealed with respect to said housing to that liquid in which the sensor device is being used is prevented from entering said device, whereby only dissolved gas and liquid vapor diffusing through said gas permeable membrane means are sensed and a signal is generated by said integrated circuitry and transmitted to a readout means remote from said pressure sensitive wafer means.

9. The improved sensor device according to claim 8 and wherein said housing means includes central opening means therethrough so that a sealed cavity is defined on one side of the pressure sensitive wafer means opposite said gas chamber so that said connecting wire means is able to connect to said integrated circuitry for said pressure sensor.

10. The improved sensor device according to claim 9 and wherein said pressure sensor is a piezoresistive pressure transducer.

11. The improved sensor device according to claim 9 and wherein said pressure sensor is a piezocapacitive pressure transducer.

12. The improved sensor device according to claim 8 and wherein said pressure sensor is a piezoresistive pressure transducer.

13. The improved sensor device according to claim 8 and wherein said pressure sensor is a piezocapacitive pressure transducer.

14. The improved sensor device according to claim 8 and wherein heating element means is provided within said housing and within said cavity to prevent the formation of condensation.

15. An improved sensor device for measuring total dissolved gas and liquid vapor, comprising:
   a) a water proof housing of generally round shape having a bottom wall with an interior surface and also having an upstanding edge wall means around the entire periphery of said bottom wall for supporting seal means, and further including pressure sensitive wafer means support operably attached to said interior surface,
   b) pressure sensitive wafer means including integrated circuitry for required signal supported in said housing on said pressure sensitive wafer means support and including mounting means for mechanical support and a pressure sensor supported on said mounting means, said pressure sensor being connected by connecting wire means for transmitting signal extending through said housing in sealed relationship thereto to an instrument and instrument readout means for indicating total dissolved gas and liquid vapor pressure,
   c) a gas porous, mechanically rigid membrane support layer overlying said pressure sensitive wafer means support, said porous membrane support layer overlying and being integrated with said pressure sensitive wafer means support and including a gas chamber of predetermined minimum volume adjacent said pressure sensitive wafer means such that said pressure sensitive wafer means is spaced from direct contact with said membrane support layer to assure that only gas pressure is sensed by said pressure sensor,
   d) gas permeable membrane means supported on and by said porous membrane support layer such that dissolved gas and liquid vapor diffuse through said gas permeable membrane means into said porous membrane support layer and into said gas chamber so that gas pressure in said porous membrane support layer reflects the total gas and liquid vapor pressure in the liquid and is sensed by said pressure sensor, and
   e) said pressure sensitive wafer means, said porous membrane support layer, and said gas permeable membrane means being liquid sealed with respect to said housing to that liquid in which the sensor device is being used is prevented from entering said device, whereby only dissolved gas and liquid vapor diffusing through said gas permeable membrane means are sensed and a signal is generated by said pressure sensor and transmitted to a readout means remote from said pressure sensitive wafer means.

16. The improved sensor device according to claim 15 and wherein said pressure sensitive wafer means includes central opening means therethrough so that a sealed cavity is defined on one side of the pressure sensitive wafer means opposite said gas chamber so that said connecting wire means is able to connect to said pressure sensor.

17. The improved sensor device according to claim 16 and wherein said pressure sensor is a piezoresistive pressure transducer.

18. The improved sensor device according to claim 16 and wherein said pressure sensor is a piezocapacitive pressure transducer.

19. The improved sensor device according to claim 15 and wherein said pressure sensor is a piezoresistive pressure transducer.

20. The improved sensor device according to claim 15 and wherein said pressure sensor is a piezocapacitive pressure transducer.

21. The improved sensor device according to claim 15 and wherein heating element means is provided within said housing and within said sealed cavity to prevent the formation of condensation.

22. An improved sensor device for measuring total dissolved gas and liquid vapor, comprising:
   a) a water proof housing of generally elongated shape having an outer cylindrical support surface and an end support surface, said housing further having bore means extending generally through the entire length thereof to define a minimum gas volume space and also having cross opening means extending between and interconnecting said cylindrical support surface and said bore means for diffusing dissolved gas and liquid vapor to said bore means, said housing also including a rear portion at the end thereof opposite said end support surface,
   b) pressure sensitive wafer means including integrated circuitry for required signal supported in said rear portion of said housing and at one end of said bore means and including mounting means for mechanical support and a pressure sensor supported on said mounting means, said pressure sensor being connected by connecting wire means for transmitting signal extending through the rear portion of said housing in sealed relationship thereto to an instrument and instrument readout means for indicating total dissolved gas and liquid vapor pressure,
   c) a gas porous, mechanically rigid membrane support layer overlying said housing cylindrical support surface and said end support surface and being integrated with said cylindrical support surface, said housing and said bore means therein defining a gas chamber of predetermined minimum volume adjacent said pressure sensitive wafer means, said pressure sensitive wafer means being spaced from direct contact with membrane support layer by said elongate housing to assure that only gas pressure is sensed by said pressure sensor,
   d) gas permeable membrane means supported on and by said porous membrane support layer such that dissolved gas and liquid vapor of a liquid diffuse through said gas permeable membrane means into said porous membrane support layer and through said cross opening means into said bore means so that gas pressure in said porous membrane support layer, cross opening means and bore means, reflects the total gas and liquid vapor pressure in the liquid, and is sensed by said pressure sensor,
   e) said pressure sensitive wafer means, said porous membrane support layer, and said gas permeable membrane means being liquid sealed with respect to said housing to that liquid in which the sensor device is being used is prevented from entering said device, whereby only dissolved gas and liquid vapor diffusing through said gas permeable membrane means are sensed and a signal is generated by said integrated circuitry and transmitted to a readout remote from said pressure sensitive wafer means.

23. The improved sensor device according to claim 22 and wherein said housing includes central opening means therethrough so that a sealed cavity is defined on one side of the pressure sensitive wafer means opposite said gas chamber so that said connecting wire means is able to connect to said integrated circuitry for said pressure sensor.

24. The improved sensor device according to claim 22 and wherein said pressure sensor is a piezoresistive pressure transducer.

25. The improved sensor device according to claim 22 and wherein said pressure sensor is a piezocapacitive pressure transducer.

26. The improved sensor device according to claim 22 and wherein heating element means is provided within said housing and within said sealed cavity to prevent the formation of condensation.

27. The improved sensor device according to claim 22 and wherein vent tube means extend from said pressure sensor to one of the liquid medium and atmosphere so that differential or gauge pressure is measured.

* * * * *